United States Patent
Katsube et al.

(10) Patent No.: US 6,946,582 B2
(45) Date of Patent: Sep. 20, 2005

(54) PROCESS FOR PRODUCING FLUOROALKYL IODIDE

(75) Inventors: Toshiyuki Katsube, Settsu (JP); Kouzou Noda, Settsu (JP); Jun Miki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/498,933

(22) PCT Filed: Nov. 20, 2002

(86) PCT No.: PCT/JP02/12094
§ 371 (c)(1),
(2), (4) Date: Jun. 16, 2004

(87) PCT Pub. No.: WO03/051800
PCT Pub. Date: Jun. 26, 2003

(65) Prior Publication Data
US 2005/0090699 A1 Apr. 28, 2005

(30) Foreign Application Priority Data
Dec. 19, 2001 (JP) .......................... 2001-385709

(51) Int. Cl.[7] .......................... C07C 21/18; C07C 69/66
(52) U.S. Cl. .................. 570/174; 570/123; 570/175; 560/129; 560/175
(58) Field of Search .................. 570/123, 174, 570/175; 560/129, 174

(56) References Cited

U.S. PATENT DOCUMENTS

| 3,829,512 A | 8/1974 | Millauer |
| 4,089,882 A | 5/1978 | Takamizawa et al. |
| 5,166,453 A | 11/1992 | Matsuda et al. |

FOREIGN PATENT DOCUMENTS

| JP | 39-18112 B1 | 8/1964 |
| JP | 39-18112 | 8/1964 |
| JP | 50-126621 | 10/1975 |
| JP | 4-69347 | 3/1992 |

OTHER PUBLICATIONS

J.Org.Chem., vol. 42, No. 11, Year 1977, p. 1985, By Rondesvtvedt, Jr.*
English translation of International Search Report for PCT/JP02/12094 dated Feb. 4, 2003.
Henne et al.; "Influence of a $CF_3$ Group on an Adjacent Double Bond"; J. Am. Chem. Soc.; vol. 72; Aug. 1950, p. 3369.
Pierce et al.; "The Synthesis of Fluorine–containing Organosilanes"; J. Am. Chem. Soc.; vol. 75; Nov. 20, 1953; pp. 5618–5620.
International Search Report for PCT/JP02/12094 dated Feb. 4, 2003.

* cited by examiner

*Primary Examiner*—Elvis Price
*Assistant Examiner*—Lansana Nyalley
(74) *Attorney, Agent, or Firm*—Sughrue Mion, PLLC

(57) ABSTRACT

The present invention provides a process for producing a fluoroalkyl iodide represented by the general formula (II):

$$Rf\text{-}CH_2CH_2I \qquad (II)$$

wherein Rf is a perfluoroalkyl or polyfluoroalkyl group comprising 1 to 20 carbons, the process comprising reacting hydrogen iodide gas with a fluoroalkene in the presence of a catalyst. The present invention also provides a process for producing a fluoroester by reacting the fluoroalkyl iodide with a carboxylate.

6 Claims, No Drawings

PROCESS FOR PRODUCING FLUOROALKYL IODIDE

TECHNICAL FIELD

The present invention relates to a process for producing a fluoroalkyl iodide using a starting material represented by the general formula (I):

Rf-CH=CH$_2$ (I)

wherein Rf is a perfluoroalkyl or polyfluoroalkyl group comprising 1 to 20 carbons. The present invention also relates to a process for efficiently producing a fluoroester usable as a starting material for water- and oil-repellents using the production process.

BACKGROUND OF THE INVENTION

In producing a fluoroester usable as a starting material for water- and oil-repellents, represented by the general formula (IV):

Rf-CH$_2$CH$_2$OCOCX=CH$_2$ (IV)

wherein Rf is a perfluoroalkyl or polyfluoroalkyl group comprising 1 to 20 carbons and X is H or CH$_3$, a process has been proposed which comprises reacting a fluoroalkyl iodide with a carboxylate represented by the general formula (III):

CH$_2$=CXCOOK (III)

wherein X is H or CH$_3$ and K is an alkali metal (Japanese Examined Patent Publication No. 18112/1964). The process, however, generates as by-products a large amount of fluoroalkenes represented by the general formula (I):

Rf-CH=CH$_2$ (I)

wherein Rf is a perfluoroalkyl or polyfluoroalkyl group comprising 1 to 20 carbons.

The fluoroalkenes can be used as a starting material for an organo-fluorosilane represented by the general formula (V):

RfCH$_2$CH$_2$SiR$_n$X$_{3-n}$ (V)

wherein Rf is a perfluoroalkyl or polyfluoroalkyl group comprising 1 to 20 carbons, R is an alkyl or aryl group and n is 0, 1, or 2 (Japanese Unexamined Patent Publication No. 126621/1975). However, the amount of the fluoroalkene required for producing the organo-fluorosilane is too small. Accordingly, the production efficiency can be improved if the excess fluoroalkene is converted into a fluoroalkyl iodide and recycled as a starting material for the above-mentioned fluoroester.

A process (dehydrohalogenation) is known which synthesizes R$_f$-CH=CH$_2$ represented by the above-described general formula (I) from a fluoroalkyl iodide (Japanese Unexamined Patent Publication No. 69347/1992). However, in the reverse reaction of adding hydrogen iodide (HI) to R$_f$-CH=CH$_2$, it is known that Rf-CHI—CH$_3$ is generally obtained as a main product following Markovnikov rule while a process for efficiently synthesizing Rf-CH$_2$CH$_2$I not following Markovnikov rule is totally unknown.

Some reactions of adding hydrogen chloride (HCl) or hydrogen bromide (HBr) to a fluoroolefin have been reported such as a process using AlBr$_3$ as a catalyst (*J. Am. Chem. Soc.*, 72, 3369 (1950)), a process using CaSO$_4$/C as a catalyst (*J. Am. Chem. Soc.*, 75, 5618 (1953)), etc.

However, the use of hydrogen chloride or hydrogen bromide poses problems: the reaction rate is extremely low; by-products such as polymers, etc. are formed. Therefore, such processes cannot be used in industrial syntheses.

DISCLOSURE OF THE INVENTION

An object of the present invention is to provide a process for producing a fluoroalkyl iodide in high efficiency using a starting material represented by the general formula (I):

Rf-CH=CH$_2$ (I)

wherein Rf is a perfluoroalkyl or polyfluoroalkyl group comprising 1 to 20 carbons.

Another object of the present invention is to provide a process for efficiently producing a fluoroester useful as a starting material for water- and oil-repellents represented by the general formula (IV) using the above-mentioned process:

Rf-CH$_2$CH$_2$OCOCX=CH$_2$ (IV)

wherein Rf is a perfluoroalkyl or polyfluoroalkyl group comprising 1 to 20 carbons and X is H or CH$_3$.

The inventors carried out intensive research to achieve the above-mentioned objects. As a result, the inventors found that a fluoroalkyl iodide can be produced by reacting a fluoroalkene with hydrogen iodide gas in the presence of a catalyst, and that a fluoroester can be efficiently produced using the production process for a fluoroalkyl iodide. The present invention has been accomplished based on these findings.

More specifically, the present invention relates to the following techniques:

Item 1. A process for producing a fluoroalkyl iodide represented by the general formula (II):

Rf-CH$_2$CH$_2$I (II)

wherein Rf is a perfluoroalkyl or polyfluoroalkyl group comprising 1 to 20 carbons, the process comprising reacting hydrogen iodide gas in the presence of a catalyst with a fluoroalkene represented by the general formula (I):

Rf-CH=CH$_2$ (I)

wherein Rf is a perfluoroalkyl or polyfluoroalkyl group comprising 1 to 20 carbons.

Item 2. A process according to Item 1, wherein the catalyst is one member selected from the group consisting of activated carbon, metal sulfates and a combination of activated carbon and metal sulfate(s).

Item 3. A process according to Item 2, wherein the metal sulfate is one or more members selected from the group consisting of potassium sulfate, sodium sulfate, calcium sulfate, magnesium sulfate and aluminium sulfate.

Item 4. A process according to Item 1, wherein the catalyst comprises one or more Lewis acids.

Item 5. A process according to Item 4, wherein the Lewis acid is one or more members selected from the group consisting of boron halides, antimony halides, tin halides, titanium halides, zinc halides, aluminum halides, gallium halides, arsenic halides, iron halides, mercury halides and zirconium halides.

Item 6. A process for producing fluoroester represented by the general formula (IV):

Rf-CH$_2$CH$_2$OCOCX=CH$_2$ (IV)

wherein Rf is a perfluoroalkyl or polyfluoroalkyl group comprising 1 to 20 carbons and X is H or CH$_3$;

the process comprising:
producing a fluoroalkyl iodide represented by the general formula (II):

$$Rf\text{-}CH_2CH_2I \qquad (II)$$

wherein Rf is a perfluoroalkyl or polyfluoroalkyl group comprising 1 to 20 carbons, by reacting hydrogen iodide gas in the presence of a catalyst with a fluoroalkene represented by the general formula (I):

$$Rf\text{-}CH\!=\!CH_2 \qquad (I)$$

wherein Rf is a perfluoroalkyl or polyfluoroalkyl group comprising 1 to 20 carbons; and reacting the thus produced fluoroalkyl iodide with a carboxylate represented by the general formula (III):

$$CH_2\!=\!CXCOOK \qquad (III)$$

wherein X is H or $CH_3$ and K is an alkali metal.

Hereinafter, the present invention will be described in more detail.

According to the invention, a fluoroalkyl iodide is produced by reacting a fluoroalkene with hydrogen iodide gas in the presence of a specific catalyst.

Examples of the catalyst include (i) a catalyst comprising one or more members selected from the group consisting of activated carbon and metal sulfates and (ii) a catalyst comprising one or more Lewis acids.

When a catalyst (i) comprising one or more members selected from the group consisting of activated carbon and metal sulfates is used, activated carbon and metal sulfates can be used alone, or in combination thereof. The activated carbon and metal sulfate(s) are used preferably in a ratio of 0.1/99.9 to 99.9/0.1 (mass %).

Examples of metal sulfates are potassium sulfate, sodium sulfate, calcium sulfate, magnesium sulfate, aluminium sulfate and the like.

When a catalyst (ii) comprising one or more Lewis acids is used, examples of Lewis acids are boron halides, antimony halides, tin halides, titanium halides, zinc halides, aluminum halides, gallium halides, arsenic halides, iron halides, mercury halides, zirconium halides and the like.

The process for producing a fluoroalkyl iodide using the above-mentioned catalyst will be described in greater detail.

According to the process of the invention, a fluoroalkyl iodide represented by the general formula (II):

$$Rf\text{-}CH_2CH_2I \qquad (II)$$

wherein Rf is a perfluoroalkyl or polyfluoroalkyl group comprising 1 to 20 carbons, is produced by reacting in the presence of the above-mentioned catalyst hydrogen iodide gas with a fluoroalkene represented by the general formula (I):

$$Rf\text{-}CH\!=\!CH_2 \qquad (I)$$

wherein Rf is a perfluoroalkyl or polyfluoroalkyl group comprising 1 to 20 carbons.

In the compound represented by the above-described general formula (I), a perfluoroalkyl group represented by Rf includes a linear or branched chain perfluoroalkyl group comprising 1 to 20 carbons. Examples thereof are $CF_3$, $C_2F_5$, (n- or iso) $C_3F_7$, (n-, iso, sec- or tert-) $C_4F_9$, $CF_3(CF_2)_m$ (m is an integer from 4 to 19), $(CF_3)_2CF(CF_2)_i$ (i is an integer from 2 to 17), etc.

Examples of polyfluoroalkyl groups include $HCF_2(CF_2)_p$ (p is an integer from 1 to 19), etc.

The reaction between a fluoroalkene represented by general formula (I) and hydrogen iodide gas can be conducted by a continuous method or a batch method. The reactor for the reaction is not limited; a gas-phase continuous reactor equipped with reaction vessel such as fixed bed reactor, fluidized bed reactor, moving bed reactor or a batch reactor may be used.

The process for reacting a halogenated fluorine compound with hydrogen iodide by a gas-phase continuous reaction comprises, for example, the steps of placing a stainless-steel reaction tube filled with the catalyst of the invention in an electric furnace, heating the catalyst layer to the reaction temperature, introducing a fluoroalkene into a vaporizer at a constant rate using a plunger pump or the like to supply the vaporized fluoroalkene to the catalyst layer together with hydrogen iodide gas whose flow rate is controlled with a mass flow controller or the like, or together with hydrogen iodide gas diluted with an inert gas, for inducing a catalytic reaction and recovering the reaction product with a subsequent trap or the like. Nitrogen, helium, argon, etc., are preferred as an inert gas for diluting hydrogen iodide gas. Favorable reaction conditions may slightly vary depending on the kind of the catalyst used; the reaction temperature is usually within the range of about 50 to about 400° C., and preferably about 100 to about 300° C. The reaction can be conducted at atmospheric pressure or at an elevated pressure. The molar ratio of the fluoroalkene to hydrogen iodide gas is preferably 1:about 0.2 to about 200. W/F (contact time) may be within the range of about 0.1 to about 10 g·sec/ml.

When the reaction is conducted by a batch method, a fluoroalkene, hydrogen iodide gas and a catalyst are placed in an autoclave or like pressure vessel, and the mixture is heated with a heater to the reaction temperature and left to stand to undergo reaction for a certain period of time with stirring. Preferable reaction conditions may vary depending on the kind of a catalyst used; the reaction temperature is usually in the range of about 50 to about 400° C. and preferably in the range of about 100 to about 300° C. The molar ratio of a fluoroalkene to hydrogen iodide gas is preferably in the range of 1:about 0.2 to about 200. The reaction time may be within the range of about 1 to about 100 hours. In the reaction atmosphere, hydrogen iodide gas alone may be used or an inert gas such as nitrogen, helium, argon and the like added to the hydrogen iodide gas.

Hereafter, a process for producing a fluoroester using a fluoroalkyl iodide obtained by the above-mentioned production process will be described.

In this process, hydrogen iodide gas and a fluoroalkene represented by general formula (I):

$$Rf\text{-}CH\!=\!CH_2 \qquad (I)$$

wherein Rf is a perfluoroalkyl or polyfluoroalkyl group comprising 1 to 20 carbons are reacted in the presence of a catalyst, to give a fluoroalkyl iodide represented by general formula (II):

$$Rf\text{-}CH_2CH_2I \qquad (II)$$

wherein Rf is a perfluoroalkyl or polyfluoroalkyl group comprising 1 to 20 carbons.

Subsequently, the obtained fluoroalkyl iodide is reacted with a carboxylate represented by general formula (III):

$$CH_2\!=\!CXCOOK \qquad (III)$$

wherein X is H or CH$_3$ and K is an alkali metal, to produce a fluoroester represented by general formula (IV):

$$Rf\text{-}CH_2CH_2OCOCX=CH_2 \qquad (IV)$$

wherein Rf is a perfluoroalkyl or polyfluoroalkyl group comprising 1 to 20 carbons and X is H or CH$_3$.

The reaction of the fluoroalkyl iodide represented by general formula (II) with the alkali metal carboxylate represented by general formula (III) can be performed by generating a mixture with, for example, an alcoholic solvent, heating the resultant solution at 125 to 200° C. for 1 to 30 hours, and then recovering the ester from the reaction mixture.

Usable as the alkali metal which forms carboxylate are lithium, sodium, potassium, etc. Among these, potassium is particularly preferable.

The reaction can be carried out by a batch method or a continuous method. The reactor for this reaction is not limited, and a gas-phase continuous reactor equipped with reaction vessel such as fixed bed, fluidized bed, moving bed, etc. may be used, or a batch reactor.

The process for producing a fluoroester using a fluoroalkyl iodide according to this invention can achieve the following remarkable effects:

(1) As compared with the addition of hydrogen chloride or hydrogen bromide, the reaction can be carried out in a shorter period of time, and with less formation of by-products and in high yield;

(2) Fluoroalkene produced as by-products can be used as the starting material for producing fluoroester, which eliminates the necessity of having a separated vessel; and (3) KI and fluoroalkene generating in the esterification reaction can be recycled as starting materials and therefore production efficiency can be improved.

BEST MODE FOR CARRYING OUT THE INVENTION

The present invention will be described below in further detail with reference to Examples and Comparative Examples. However, the scope of the invention is not limited to these Examples.

EXAMPLE 1

198 g of CF$_3$(CF$_2$)$_7$CH=CH$_2$ and 5 g of AlI$_3$ were charged into a 200-ml stainless-steel autoclave and displacement of the atmosphere with nitrogen was repeated 5 times by vacuum evacuation and charging with nitrogen gas while cooling the autoclave with dry ice/acetone. The oxygen concentration inside the system was not more than 1 ppm and the moisture content was not more than 1 ppm. Thereafter, nitrogen was removed by evacuation and 11 g of hydrogen iodide gas was charged therein. Heating was carried out with stirring for two hours at 130° C. After cooling, the liquid in the autoclave was sampled, and GC analysis (gas chromatography analysis) and GC/MS analysis (gas chromatography/mass analysis) were performed. CF$_3$(CF$_2$)$_7$CH$_2$CH$_2$I was produced at a conversion rate of 2% and at a selectivity of 100%.

EXAMPLE 2

The same process as in Example 1 was conducted except that 41 g of CF$_3$(CF$_2$)$_7$CH=CH$_2$, 12 g of CaSO$_4$/C (25/75 mass %) instead of AlI$_3$, and 12 g of hydrogen iodide gas were used. CF$_3$(CF$_2$)$_7$CH$_2$CH$_2$I was produced at a conversion rate of 60% and at a selectivity of 100%.

EXAMPLE 3

The same process as in Example 1 was conducted except that 41 g of CF$_3$(CF$_2$)$_7$CH=CH$_2$, 12 g of activated carbon instead of AlI$_3$, and 12 g of hydrogen iodide gas were used. CF$_3$(CF$_2$)$_7$CH$_2$CH$_2$I was produced at a conversion rate of 20% and at a selectivity of 100%.

EXAMPLE 4

The same process as in Example 1 was conducted except that 41 g of CF$_3$(CF$_2$)$_7$CH=CH$_2$, 12 g of CaSO$_4$ instead of AlI$_3$, and 12 g of hydrogen iodide gas were used. CF$_3$(CF$_2$)$_7$CH$_2$CH$_2$I was produced at a conversion rate of 1% and at a selectivity of 100%.

EXAMPLE 5

The same process as in Example 1 was conducted except that 41 g of CF$_3$(CF$_2$)$_7$CH=CH$_2$, 12 g of CaSO$_4$/C (25/75 mass %) instead of AlI$_3$, and 24 g of hydrogen iodide gas were used. CF$_3$(CF$_2$)$_7$CH$_2$CH$_2$I was produced at a conversion rate of 90% and at a selectivity of 100%.

EXAMPLE 6

The catalyst was separated from the reaction liquid obtained in Example 5 by filtration, and the unreacted olefin was removed with an evaporator, giving 47.5 g of solid CF$_3$(CF$_2$)$_7$CH$_2$CH$_2$I. A 200-ml SUS autoclave was charged with 47.5 g (0.082 mol) of the obtained solid CF$_3$(CF$_2$)$_7$CH$_2$CH$_2$I, 9.9 g (0.090 mol) of potassium acrylate, 25 g of t-butanol (solvent), 0.6 g of hydroquinone (polymerization inhibitor) and 0.01 g of hydroquinone monomethyl ether (polymerization inhibitor), and a reaction was then carried out with stirring at 180° C. for 6 hours. As a result, CF$_3$(CF$_2$)$_7$CH$_2$CH$_2$OCOCH=CH$_2$ was obtained at a CF$_3$(CF$_2$)$_7$CH$_2$CH$_2$I conversion rate of 99% and at a selectivity of 88%. The results of NMR analysis revealed that polymerization of CF$_3$(CF$_2$)$_7$CH$_2$CH$_2$OCOCH=CH$_2$ was not detected.

COMPARATIVE EXAMPLE 1

637 g of CF$_3$(CF$_2$)$_7$CH=CH$_2$ was charged into a 200-ml quartz vessel and the interior of the system was then purged with N$_2$, resulting in oxygen concentration of 8 ppm. The vessel was UV irradiated with a high pressure mercury-vapor lamp (100W, manufactured by SEN LIGHTS CORPORATION, HL100CH-5-type) while introducing (bubbling) HI into the vessel, and the reaction was conducted for 1 hour. The amount of HI introduced was 22.4 g. The liquid in the vessel was sampled, and GC analysis (gas chromatography analysis) and GC/MS analysis (gas chromatography/mass analysis) were carried out. As a result, a conversion rate was 2%, a CF$_3$(CF$_2$)$_7$CH$_2$CH$_2$I selectivity was 25% and a CF$_3$(CF$_2$)$_7$CHICH$_3$ selectivity was 75%.

COMPARATIVE EXAMPLE 2

The same process as in Example 1 was conducted except that 41 g of CF$_3$(CF$_2$)$_7$CH=CH$_2$, 12 g of CaSO$_4$/C (25/75 mass %) instead of AlI$_3$, and 3.4 g of hydrogen chloride gas instead of 11 g of hydrogen iodide gas were used. CF$_3$(CF$_2$)$_7$CH$_2$CH$_2$Cl was produced at a conversion rate of 1.7% and at a selectivity of 100%.

COMPARATIVE EXAMPLE 3

The catalyst was separated from the reaction liquid obtained in Comparative Example 2 by filtration, and the unreacted olefin was removed with an evaporator, giving 0.9 g of liquid $CF_3(CF_2)_7CH_2CH_2Cl$. This process was repeatedly conducted. Thereafter, a 200-ml SUS autoclave was charged with 39.5 g (0.082 mol) of the obtained liquid $CF_3(CF_2)_7CH_2CH_2Cl$, 9.9 g (0.090 mol) of potassium acrylate, 25 g of t-butanol (solvent), 0.6 g of hydroquinone (polymerization inhibitor) and 0.01 g of hydroquinone monomethyl ether (polymerization inhibitor), and a reaction was then conducted with stirring at 180° C. for 6 hours. As a result, $CF_3(CF_2)_7CH_2CH_2OCOCH=CH_2$ was obtained at a $CF_3(CF_2)_7CH_2CH_2Cl$ conversion rate of 12% and at a selectivity of 80%. The results of NMR analysis revealed that a polymer generated by polymerization of $CF_3(CF_2)_7CH_2CH_2OCOCH=CH_2$ was produced at a selectivity of 5%.

INDUSTRIAL APPLICABILITY

The present invention provides a production process for producing, in high yield, a fluoroalkyl iodide represented by the general formula (II):

$$Rf\text{-}CH_2CH_2I \qquad (II)$$

wherein Rf is a perfluoroalkyl or polyfluoroalkyl group comprising 1 to 20 carbons, by reacting a fluoroalkene with hydrogen iodide gas in the presence of a catalyst.

Moreover, according to the present invention, a fluoroester usable as a starting material for water- and oil-repellents can be produced in a shorter period of time and with less formation of by-products by applying the above-mentioned production process for the fluoroalkyl iodide. Additionally, fluoroalkene can be recycled as the starting material and therefore production efficiency can be improved.

What is claimed is:

1. A process for producing a fluoroalkyl iodide represented by the general formula (II):

$$Rf\text{-}CH_2CH_2I \qquad (ii)$$

wherein Rf is a perfluoroalkyl or polyfluoroalkyl group comprising 1 to 20 carbons, the process comprising reacting hydrogen iodide gas in the presence of a catalyst with a fluoroalkene represented by the general formula (I):

$$Rf\text{-}CH=CH_2 \qquad (I)$$

wherein Rf is a perfluoroalkyl or polyfluoroalkyl group comprising 1 to 20 carbons.

2. A process according to claim 1, wherein the catalyst is one member selected from the group consisting of activated carbon, metal sulfates and a combination of activated carbon and metal sulfate(s).

3. A process according to claim 2, wherein the metal sulfate is one or more members selected from the group consisting of potassium sulfate, sodium sulfate, calcium sulfate, magnesium sulfate and aluminium sulfate.

4. A process according to claim 1, wherein the catalyst comprises one or more Lewis acids.

5. A process according to claim 4, wherein the Lewis acid is one or more members selected from the group consisting of boron halides, antimony halides, tin halides, titanium halides, zinc halides, aluminum halides, gallium halides, arsenic halides, iron halides, mercury halides and zirconium halides.

6. A process for producing fluoroester represented by the formula (IV):

$$Rf\text{-}CH_2CH_2OCOCX=CH_2 \qquad (IV)$$

wherein Rf is a perfluoroalkyl or polyfluoroalkyl group comprising 1 to 20 carbons and X is H or $CH_3$;

the process comprising:

producing a fluoroalkyl iodide represented by the general formula (II):

$$Rf\text{-}CH_2CH_2I \qquad (II)$$

wherein Rf is a perfluoroalkyl or polyfluoroalkyl group comprising 1 to 20 carbons, by reacting hydrogen iodide gas in the presence of a catalyst with a fluoroalkene represented by the general formula (I):

$$Rf\text{-}CH=CH_2 \qquad (I)$$

wherein Rf is a perfluoroalkyl or polyfluoroalkyl group comprising 1 to 20 carbons; and reacting the thus produced fluoroalkyl iodide with a carboxylate represented by the general formula (III):

$$CH_2=CXCOOK \qquad (III)$$

wherein X is H or $CH_3$ and K is an alkali metal.

* * * * *